United States Patent
Knepp et al.

(10) Patent No.: US 6,277,828 B1
(45) Date of Patent: Aug. 21, 2001

(54) PHARMACEUTICAL FORMULATIONS OF NERVE GROWTH FACTOR

(75) Inventors: Victoria M. Knepp, Sunnyvale; Deborah M. Lidgate, Los Altos; Richard Maskiewicz, Sunnyvale; Leo Gu, Saratoga, all of CA (US)

(73) Assignee: Syntex (U.S.A.) Inc., Palo Alto, CA (US)

( * ) Notice: Subject to any disclaimer, the term of this patent is extended or adjusted under 35 U.S.C. 154(b) by 0 days.

(21) Appl. No.: 08/109,798

(22) Filed: Aug. 20, 1993

(51) Int. Cl.[7] .............................. A61K 38/18; C07K 14/48
(52) U.S. Cl. .................................. 514/21; 514/2; 514/12; 424/198.1; 424/583; 530/399; 530/839
(58) Field of Search ..................................... 514/2, 12, 21; 424/583; 530/399, 839

(56) References Cited

U.S. PATENT DOCUMENTS

| | | | |
|---|---|---|---|
| 5,096,885 | 3/1992 | Pearlman et al. | 514/12 |
| 5,210,185 * | 5/1993 | Della Valle et al. | 530/399 |

FOREIGN PATENT DOCUMENTS

| | | | |
|---|---|---|---|
| 0 267 015 | 5/1988 | (EP) | A61K/37/02 |
| 0308238 * | 3/1989 | (EP) | A61K/37/02 |

OTHER PUBLICATIONS

Gregouadis et al (1993) Trends in Biotech. 11:440–442.*
Calbiochem Catalog (1992), p. 219.*
Diem et al. (eds.) (1970) "Scientific Tables", Ciba–Geigy, Ltd., Basle, Switzerland, pp. 271–273, 280–281, & 528–529.*

M.J. Pikal, "Freeze–Drying of Proteins–Part II: Formulation Selection", *BioPharm*, 26–30, (Oct. 1990).

Arakawa, et al., "Stabilization of Protein Structure by Sugars", *Biochemistry* 1982, 21, 6536–6544.

Wang, et al., "Parenteral Formulations of Proteins and Peptides: Stability and Stabilizers", *J. Parenter. Sci. Tech.*, 42, S3–S26 (1988).

Pignatti, et al., "Solution Properties of β Nerve Growth Factor Protein and Some of its Derivatives", *J. Neurochem.*, 1975 vol. 25, pp. 155–159.

* cited by examiner

*Primary Examiner*—Anthony Caputa
*Assistant Examiner*—Karen A. Canella
(74) *Attorney, Agent, or Firm*—Heller Ehrman White & McAuliffe LLP

(57) ABSTRACT

Stable, aqueous pharmaceutical formulations of human nerve growth factor (NGF) in aqueous isotonic solutions, buffered to maintain the pH from about 4.5 to about 6.0, and optionally containing a carrier such as human serum albumin are provided. Also provided are aqueous NGF formulations suitable for lyophilization and subsequent reconstitution in which rhNGF is admixed with sugars, optionally HSA, and buffer. The formulations are useful for the treatment of Alzheimer's disease and other neuronal disorders.

11 Claims, No Drawings

PHARMACEUTICAL FORMULATIONS OF NERVE GROWTH FACTOR

TECHNICAL FIELD OF THE INVENTION

This invention relates to pharmaceutical formulations of nerve growth factor. This invention also relates to formulations of nerve growth factor suitable for lyophilization.

BACKGROUND OF THE INVENTION

Numerous polypeptides and proteins regulate the growth or survival of cells; such molecules are termed "growth factors". Examples of growth factors include epidermal growth factor (EGF), acidic and basic fibroblast growth factor (aFGF and bFGF), platelet derived growth factor (PDGF), ciliary neurotrophic factor (CNTF), and nerve growth factor (NGF). Of these, NGF was the first to be identified and characterized (Levi-Montalcini, R., et al., *J. Exp. Zool.*, 116:321, 1951).

NGF promotes the survival and activity of certain types of neuronal cells. In addition, NGF promotes the differentiation of premature neuronal cells into post-mitotic mature neurons.

Purification of NGF from mouse submaxillary gland resulted in the identification of a complex comprising three subunits, , β, and γ. All of the neurotrophic activity of NGF is presumed to reside in the β subunit, a 118 amino acid protein having a molecular weight of about 13,000 Da (Varon, S., et al., *Proc. Natl. Acad. Sci. USA,* 57:1782–1789, 1967; Greene, L. A., et al., *Neurobiol.,* 1:37–48, 1971). In solution, β subunits form dimers of molecular weight about 26,500 Da.

NGF has been suggested to be effective for treating certain degenerative diseases of both the peripheral and central nervous systems. It has been suggested that the administration of NGF may be beneficial in treating diseases in which a deficiency of NGF, abnormalities of its receptor, or changes in its transport or intracellular processing lead to a decrease in neuronal function, atrophy or even cell death. Such diseases include hereditary sensory and motor neuropathies, hereditary and sporadically occurring system degeneration, amyotrophic lateral sclerosis, Parkinson's disease, and Alzheimer's disease (Goedert, M., et al., *Mol. Brain Res.,* 1:85–92, 1986; Mobley, W. C., et al., *Soc. Neurosci. Abstr.,* 13:186, 1987; Mobley, W. C., et al., *Soc. Neurosci. Abstr.,* 4:302, 1988; Hefti, F., et al., *Ann. Neurol.,* 20:275–281, 1986). NGF is also thought to decrease neuron cell death after exposure to certain toxins, such as 6-hydroxy-dopamine, (Aloe, L., *Arch. Ital. Biol.,* 113:326–353, 1975), vinblastine and colchicine (Menesini-Chen, M. G., et al., *Proc. Natl. Acad. Sci. USA,* 74:5559–5563, 1977; Johnson, E. M., *Brain Res.,* 141:105–118, 1978) and capsaicin (Otten, U., *Nature,* 301:515–577, 1983).

The high expression of NGF mRNA in the hippocampus, an area associated with memory and learning, suggests that clinical application of NGF may be effective for the treatment of dementia (Kaisho, Y., et al., *Biochem. Biophys. Res, Comm.,* 174:379–385, 1991). The intraventricular administration of NGF has been reported to prevent the death of basal forebrain cholinergic neurons after axotomy suggesting that NGF may be effective in promoting cell survival after injury. (Hefti, F., *J. Neurosci.,* 6:2155–2162, 1986; Williams, L., et al., *Proc. Natl. Acad. Sci. USA,* 83:9231–9235, 1986; Kromer, L., *Science,* 235:214–216, 1987).

The use of NGF for therapy poses significant problems. These problems are associated with 1) maintaining the bioactivity of the NGF, which may be altered during manufacturing, purification, or storage; and 2) administering NGF, a relatively large, hydrophilic molecule, so it reaches the active site in sufficient amounts to be effective. The bioactivity of NGF, like other proteins, is dependent on its secondary and tertiary structure. The β subunit of NGF has three internal disulfide bonds, which are thought to be important for bioactivity (Kanaya, E., et al., *Gene,* 83:65–74, 1989; Iwane, M., et al., *Biochem. Biophys. Res. Comm.,* 171:116–122, 1990; Hu, G.-L. and Neet, K. E., *Gene,* 70:57–65, 1988). In addition, to the extent that any of the protein is denatured, the effective amount of biologically active NGF is diminished. Protein integrity must therefore be maintained during manufacture and storage as well as during administration. Proteins are particularly prone to degradation at elevated temperatures.

Lower temperatures generally decrease protein degradation. However, it is more economical to store the protein at room temperature, i.e., about 25° C., rather than at refrigerated temperatures of about 4° C. Therefore, formulation stability is desirable for storage at either room temperature or refrigeration at approximately 4° C.

In addition to problems of stability, NGF, like many other proteins, binds nonspecifically to surfaces. Such nonspecific binding may occur to a variety of materials including glass and plastics, for example polyethylene or polypropylene. These materials may be in the form of vials, tubing, syringes, implantable infusion devices or any other surface which may come in contact with NGF during its manufacture, storage or administration.

Other difficulties in administering proteins such as NGF as therapeutics are poor absorption by the body and degradation by stomach acids. Oral administration is therefore generally unsuitable. Injections and infusion of such proteins may be necessary to overcome such absorption barriers.

Injection is useful when the site of treatment is readily accessible. However, if the site is relatively inaccessible such as the CNS, continuous infusion may be more practical for long term administration. Such administration has been impractical due to various complications. For example, continuous infusion may be achieved by implanting NGF pumps into the brain, but long term exposure of a protein to body temperature often causes degradation of the protein. Also, there may be additional losses due to protein adsorption to the pump chamber over time.

In addition to the problems associated with the administration of NGF, there are also problems associated with its long term storage from the time of manufacture to administration. Lyophilization is one method of long term storage of biological proteins, impeding degradation, aggregation, and/or nonspecific adsorption. However, the lyophilization process itself presents difficulties. As the volume of liquid decreases during the freezing process, the effective salt concentration increases dramatically, which may denature the protein, reducing effective therapeutic activity upon reconstitution. In addition, formation of ice crystals during the freezing process may cause denaturation and also decrease the effective amount of bioactive NGF available. The formulation then must be such as to prevent salt concentration fluctuations and minimize formation of ice crystals.

One object of this invention is to provide aqueous formulations of NGF which retain bioactivity for at least one month over a temperature range from about 4° C. to about 40° C.

Still another object of the present invention is to provide formulations of NGF in which bioactivity is maintained after lyophilization and reconstitution.

It is still another object of the invention to provide methods of storing biologically active NGF in solution.

SUMMARY OF THE INVENTION

This invention provides stable formulations of nerve growth factor, capable of being stored at sub-ambient, ambient and elevated temperatures without substantial losses in the amount or activity of protein. The formulations comprise aqueous solutions of:

(a) nerve growth factor;
(b) optionally, a biologically acceptable, water soluble carrier;
(c) a sufficient amount of biologically acceptable salt to maintain isotonicity;
(d) a buffer to maintain the pH of the formulation from about 4.5 to about 6.0; and
(e) water.

In another aspect, this invention provides pharmaceutical formulations of NGF suitable for lyophilization.

The pharmaceutical formulations of this invention suitable for lyophilization comprise aqueous solutions of:

(a) nerve growth factor;
(b) a biologically acceptable bulking agent;
(c) buffer to maintain the pH of the formulation from about 5.5 to about 6.5;
(d) optionally, a biologically acceptable, water soluble carrier; and
(e) water.

Further embodiments of this invention are the lyophilized formulations from which the water has been substantially removed. Upon reconstitution with a reconstituting vehicle, optionally including a biologically acceptable carrier, the lyophilized formulations of this invention are suitable for administration to patients in need of therapy.

This invention also provides a method of storing NGF in the aqueous formulations of this invention at temperatures from about 4° C. to about 40° C.

Another embodiment of this invention is a method of treating neuronal dysfunction in humans comprising the administration of a therapeutically effective amount of an NGF formulation of this invention.

DETAILED DESCRIPTION OF THE INVENTION

The development of stable parenteral dosage forms for NGF requires the evaluation of a multitude of factors, including route of administration, adsorptive interactions, and compatibility with processing equipment and potential delivery devices. A further consideration is the stability of NGF in aqueous formulations at sub-ambient, ambient and elevated temperatures. One embodiment of this invention is a formulation of NGF in an aqueous solution which exhibits stability at a range of temperatures, and particularly at elevated (at least about 40° C.) temperatures. This formulation comprises an aqueous solution of NGF, a salt and a buffer, having a pH of about 4.5 to about 6.0. The formulation may further optionally comprise a carrier. This combination of ingredients surprisingly provides very favorable characteristics to the solution, particularly as related to stability at elevated temperatures. Also provided is a formulation of NGF suitable for lyophilization. This invention also provides a method of storing NGF.

As used herein, "biologically acceptable" applies to materials characterized by the absence of adverse biological effects in vivo. "Room temperature" is between about 22° C. to about 25° C. "Body temperature" is between about 36° C. to about 40° C. "Lyophilizable formulation" refers to an aqueous formulation of NGF which may be freeze dried to a moisture content of less than about 2% and which retains at least about 70% of the initial NGF bioactivity upon reconstitution. "Isotonic" refers to a solution having approximately the same osmotic pressure as blood serum, about 300 millimols per liter.

A "carrier" is any biologically acceptable emulsifier, dispersing agent, surfactant, or protein which decreases adsorption of NGF to a surface.

"NGF" denotes any form of nerve growth factor, preferably the $\beta$ subunit of nerve growth factor, which exhibits biological activity and binds to the NGF receptor. The term NGF also includes hybridized and modified forms of NGF which bind to the NGF receptor and retain NGF bioactivity. Modified forms of NGF may include fusion proteins such as those described in Iwai, S., et al., *Chem. Pharm. Bull.*, 34:4724–4730, 1986 and Kanaya, E., et al., *Gene*, 83:65–74, 1989, and NGF fragments and hybrids in which certain amino acids have been deleted or replaced while maintaining sufficient NGF bioactivity and receptor binding to provide therapeutic activity.

The preferred form of NGF is human NGF (hNGF). The most preferred form of hNGF is recombinant hNGF (rhNGF). Methods of obtaining NGF suitable for use in the formulations of this invention are known to those skilled in the art. For example, suitable rhNGF may be produced by a baculovirus expression system (Barnett, J., et al., *Exp. Neurol.*, 110:11–24, 1990; EPO 370,171), a yeast expression system (Kanaya, E., et al., *Gene* 83:65–74, 1989), a mammalian cell (CHO) expression system (Iwane, M., et al., *Biochem. Biophys. Res. Comm.*, 171:116–122, 1990), a COS expression system (Bruce, G., et al., *Neurobiol. Aging*, 10:89–94, 1989), or bacterial expression system (Hu, G.-L., et al., *Gene*, 70:57–65, 1988). The NGF should be at least 65% pure; preferably at least 85% pure; more preferably at least 95% pure; and most preferably at least 98% pure. The purity of isolated NGF for use in the formulations may be determined by silver-stained SDS-PAGE or other means known to those skilled in the art.

In the aqueous NGF formulations provided, NGF is present in therapeutically effective amounts. Preferably NGF comprises from about 0.0001 to about 0.125% by weight of the aqueous composition which corresponds to between about 1 to about 1250 µg/ml. More preferably NGF is present in an amount from about 0.001 to about 0.10% by weight (10 to 1000 µg/ml) of the aqueous formulation. Even more preferably NGF is present in an amount from about 0.01 to about 0.10% (100 to 1000 µg/ml) by weight of the aqueous formulation. Most preferably NGF is present in an amount from about 0.01 to about 0.05% (100 to 500 µg/ml) by weight of the aqueous formulation.

The aqueous NGF formulations optionally include carriers. The presence of the carrier in the formulation reduces or prevents NGF adsorption to various surfaces. The need for carrier depends upon the concentration of NGF in the aqueous composition. At sufficiently high (greater than about 500 µg/ml) NGF concentrations, enough NGF remains in solution to offset that which is lost due to surface adsorption. Suitable carriers include, but are not limited to, polysorbates such as Tween® 80, poloxamers such as Pluronic® F68, and proteins such as serum albumin. The preferred carrier is a protein. Human serum albumin (HSA) is particularly preferred. The weight ratio of NGF to carrier is from about 0.0001:1 to about 1:1. A more preferred weight ratio is from about 0.01:1 to about 1:1. The most preferred weight ratio of NGF to carrier is about 0.01:1 to about 0.5:1. Accordingly, when HSA is used as the carrier, the preferred concentration of HSA is from about 0.1 to about 1.25% by weight (i.e., 1 to 12.5 mg/ml) of the aqueous formulation. A preferred formulation is about 0.3 to 0.7% HSA by weight of the aqueous formulation, more preferably about 0.4 to 0.6% HSA by weight of the aqueous formulation. The most preferred formulation is about 0.5% (i.e., 5 mg/ml) HSA by weight of the aqueous formulation.

The NGF formulation also contains a sufficient amount of biologically acceptable salt to maintain fluid tonicity. The salt also acts to maintain the NGF in solution. Preferably, the NGF formulation contains sufficient salt to be isotonic, within physiologically acceptable limits, with human blood or cerebral spinal fluid. The preferred salt is sodium chloride (NaCl) but other biologically acceptable salts may be used, such as potassium chloride (KCl), calcium chloride ($CaCl_2$) and magnesium chloride ($MgCl_2$). The salt may be one salt or a combination of salts. A preferred formulation comprises about 0.5 to 1.0% (i.e., 5 to 10 mg/ml) salt by weight of the aqueous formulation. A more preferred formulation comprises about 0.6 to 0.9% salt by weight of the formulation. More preferably, the formulation comprises about 0.7 to 0.9% salt by weight of the aqueous formulation. The most preferred formulation comprises about 0.87% (i.e., 8.7 mg/ml) salt by weight of the aqueous formulation.

The NGF formulation further contains a biologically acceptable buffer to maintain the pH during storage. We have found that NGF is more stable at low pH. The preferred stable NGF formulation is buffered with a biologically acceptable buffer to a pH between about 4.5 to about 6.0 and more preferably to between about 5.0 to about 5.4. The most preferred pH of the formulation is about 5.2. The preferred buffer is citric acid, but other buffers capable of maintaining the pH within the desired range are also envisioned. Other suitable buffers include acetic acid/acetate and maleic acid/maleate. The preferred amount of buffer will vary depending on the type of buffer used and its buffering capacity. The buffer should be present in the formulation in an amount sufficient to maintain the final pH of the formulation in the preferred pH range. The preferred concentration of buffer for stable NGF formulations is about 0.01 to about 0.3% by weight of the aqueous formulation (0.1 to 3.0 mg/ml), a more preferred concentration is about 0.1 to about 0.25% buffer by weight of the aqueous formulation (1.0 to 2.5 mg/ml), and the most preferred buffer concentration is about 0.2% buffer by weight of the aqueous formulation (2.0 mg/ml).

The formulation comprises water in an amount sufficient to achieve the appropriate concentration of formulation components.

Preferred stable aqueous formulations of NGF comprise about 1 to 1250 µg/ml NGF, 1 to 12.5 mg/ml HSA, 5 to 10 mg/ml NaCl, 0.2 to 3.0 mg/ml citric acid and water, wherein the pH of the formulation is adjusted to about 4.5 to about 6.0, more preferably from about 5.0 to about 5.4. The most preferred stable formulations of NGF comprise 10 to 500 µg/ml NGF, 5 mg/ml HSA, 8.7 mg/ml NaCl, 2.1 mg/ml citric acid and water, wherein the pH of the formulation is adjusted to about 5.2.

The lyophilized formulations of this invention are particularly useful for providing long term storage of NGF, especially at elevated temperatures. The lyophilizable formulations of this invention comprise NGF, a biologically acceptable bulking agent, a buffer to maintain the pH of the formulation from about 5.5 to about 6.5, biologically acceptable salt, optionally, a biologically acceptable, water soluble carrier, and water.

NGF is present in the lyophilizable formulations over the same concentration range as in the aqueous formulations. The bulking agent generally provides mechanical support by allowing the matrix to maintain its conformation during and after the freeze-drying process. One or more sugars may be used as the bulking agent. Sugars, as used herein, include, but are not limited to, monosaccharides, oligosaccharides and polysaccharides. Examples of suitable sugars include, but are not limited to, fructose, glucose, mannose, sorbose, xylose, maltose, lactose, sucrose, and dextran. Sugar also includes sugar alcohols, such as mannitol, sorbitol, inositol, dulcitol, xylitol and arabitol. Mixtures of sugars may also be used in accordance with this invention.

A preferred bulking agent comprises a combination of sugars. The preferred bulking agent is a combination of sucrose and mannitol. Without being bound by theory, sucrose is thought to form an amorphous glass upon freezing and subsequent lyophilization, allowing for potential stability enhancement of the protein (e.g. prevention of aggregation) by forming a molecular dispersion of NGF in a rigid glass. Stability may also be enhanced by virtue of the sugar acting as a replacement for the water lost upon lyophilization. The sugar molecules rather than the water molecules become bonded to the protein through hydrogen bonds. Mannitol when mixed in a 1:1 mass ratio with sucrose (which has a glass transition temperature of −36° C.) raises the glass transition temperature of the formulation by 5° C. to −31° C. This considerably shortens the primary drying time of the formulation during lyophilization, while still allowing for an amorphous, glassy formulation matrix, and thus is considered an advantage in a large scale manufacturing setting. Other bulking agents which also possess these characteristics may be substituted for one or both of these sugars.

The formulations of this invention which are to be lyophilized preferably have a higher pH than the formulations which are not lyophilized or that are reconstituted. The bulking agents (sugars) which are present in the lyophilizable formulations of the invention are generally more stable at higher pH. Preferably the pH of the formulation prior to lyophilization is between about 5.5 to about 6.5. More preferably the pH of the lyophilizable NGF formulation is between about 5.8 to about 6.2. The pH of the most preferred lyophilizable NGF formulation is about 6.0. When sucrose is present as the bulking agent, the preferred pH of the lyophilizable formulation is about 6.0 since at acidic pH, sucrose, a non-reducing disaccharide, hydrolyzes to the reducing sugars D-fructose and D-glucose. Citrate is the most preferred buffer for lyophilizable NGF formulations but other biologically acceptable buffers may be used, such as maleate. Buffers other than acetate are preferred because of the tendency of acetic acid to volatize during lyophilization. It should be recognized that adjustment of the final pH with acid or base may be necessary. Any loss in long-term stability of aqueous NGF due to the higher pH of about 6.0 is likely to be overcome by the increase in stability associated with the NGF being lyophilized.

Ideally, the choice of buffer takes into account potential pH shifts during lyophilization caused by sequential crystallization of buffer components. For example, with phosphate buffers, the basic component has a higher eutectic point than the acidic component, hence it crystallizes out first and the pH drops. Citrate buffer is preferred because it is thought that both buffer components have about the same eutectic point, resulting in very little pH fluctuation as the temperature drops. Other suitable buffers would have components with the same, or similar eutectic points.

The lyophilizable formulations also comprise a biologically acceptable salt. The salt, which may be selected from the same salts useful in the aqueous formulations, is present in the lyophilizable formulation at the same or reduced concentrations as that in the aqueous formulations. Because the salt concentration may increase during lyophilization, it may be desirable to reduce the concentration of salt present in the lyophilizable formulations to prevent protein denaturation. Reductions in salt concentration in the lyophilizable formulation may be compensated for during reconstitution so as to provide a final formulation sufficiently isotonic to be suitable for administration into an individual.

Optionally, the lyophilizable formulations comprise a biologically acceptable water soluble carrier. The carriers and the concentration of carriers which may be used in the lyophilizable formulations of this invention are the same as those that are suitable for use in the aqueous formulations of this invention.

The preferred lyophilizable formulations comprise about 1 to 1250 µg/ml NGF, 15 to 45 mg/ml sucrose, 15 to 45 mg/ml mannitol, 7 to 9 mg/ml NaCl and 0.1 to 0.7 mg/ml citric acid at a pH of about 5.5 to about 6.5. The most preferred lyophilizable formulations of NGF comprise 100 to 1250 µg/ml NGF, 30 mg/ml sucrose, 30 mg/ml mannitol, 5 mg/ml human serum albumin, 8.7 mg/ml NaCl and 0.3 mg/ml citric acid. The most preferred pH of the lyophilizable formulation is about 6.0.

The lyophilizable formulations of this invention are lyophilized to a residual moisture content of less than about 2%, however, formulations which retain NGF biological activity at higher or lower amounts of moisture content are also contemplated.

The preferred lyophilized formulation comprises 0.001 to 1.25 parts nerve growth factor, 30 to 90 parts sugar, and less than about 1 part water.

The lyophilized NGF formulation is reconstituted with a diluent containing citric acid and sodium chloride such that the resulting reconstituted formulation is similar to the liquid aqueous formulation, i.e. about 1 to 1250 µg/ml NGF, 1 to 12.5 mg/ml HSA, 5 to 10 mg/ml NaCl, 0.2 to 3.0 mg/ml citric acid, 1.5 to 30 mg/ml sucrose and 1.5 to 30 mg/ml mannitol, pH 5.2.

The lyophilized NGF formulation of this invention is also useful as a component of a kit to provide a convenient and economical way of providing stable lyophilized NGF in a form which may be rapidly and easily reconstituted in an appropriate vehicle for administration to a patient in need of treatment. In addition to the lyophilized NGF formulation, the kits of this invention also comprise a reconstituting vehicle. The reconstituting vehicle comprises sterile water and a sufficient amount of salt to make the final reconstituted formulation essentially isotonic. The reconstituting vehicle may further comprise additional buffer. The total volume of reconstituting vehicle present in the kit should be sufficient to achieve a final NGF concentration suitable for administration to an individual in need of treatment. In a preferred embodiment of this invention a kit comprising two vials is provided. One vial comprises the sterile lyophilized NGF formulation of this invention and a second vial comprises sterile reconstituting vehicle. To use the kit, an appropriate amount of reconstituting vehicle is transferred to the vial comprising the lyophilized NGF formulation. Upon dissolution of the lyophilized formulation, the reconstituted formulation may be immediately administered to the patient.

Because of the long term stability of the reconstituted formulation of this invention it is also possible to prepare enough reconstituted formulation to provide multiple doses.

The formulations of this invention are useful for treating individuals with conditions responsive to NGF therapy. Such therapy may be useful to treat neuronal dysfunctions involving neuronal injury or degeneration of NGF responsive neurons. NGF may be particularly useful for treating disease due to loss of central cholinergic neurons such as Alzheimer's disease. NGF as a treatment of Alzheimer's disease and other forms of dementia is described in EP 0 370 171, incorporated herein by reference.

The formulations of the invention as treatments for dementia may be administered by any of a variety of routines depending on the specific end use. The most suitable route will depend upon the use and the subject involved.

To overcome the difficulties presented by the blood-brain barrier, NGF may be administered into the CNS by direct intraventricular injections or via drug impregnated implants or pumps. Another administration route is by continuous infusion through an intracerebroventricular cannula device. Alternatively, conjugation of the NGF with carrier molecules, such as transferrin, may be necessary to penetrate the blood-brain barrier.

A therapeutically effective amount of NGF is expected to be from about 0.001 to about 0.5 mg per day, preferably from about 0.01 to about 0.10 mg per day, most preferably from about 0.02 to about 0.06 mg per day. The exact dose and regimen for administration will depend upon many factors, such as the route of administration and the degree of affliction of the individual receiving treatment.

Assay Procedures
Identification and Quantitation of NGF Using Reverse Phase HPLC NGF was identified and quantified by analyzing 100 µl samples with a reverse phase HPLC (Hewlett Packard HP 1090 Liquid Chromatograph) equipped with a 4–6 mm×25 cm L Dynamax 300 Å 5 µm Analytical Reversed-Phased column with a Dynamax 300 Å 5 µm 4.6 mm×1.5 cm guard column and a diode array UV detector set at 220 nm. The mobile phases were (A) 0.1% trifluroacetic acid in water and (B) 0.1% trifluroacetic acid in acetonitrile where the gradients changed from 25% (B) to 60% (B) in 45 minutes with a flow rate of 0.5 ml/min at a pressure of 1700–2000 psi at ambient temperature.

Identification of NGF was established by comparing its retention time in the sample with the respective retention time of freshly prepared calibrated standard NGF solutions made from NGF from the same lot. The quantity of NGF in the samples was calculated by comparison to a standard curve obtained with serial dilutions of known concentrations.

Determination of NGP Concentration (µg/ml) by ELISA

NGF concentrations were also assayed by ELISA. Both standards and samples were assayed in triplicate. Each plate contained a complete standard curve of NGF and reference blanks without NGF.

After 100 µl of coating antibodies (mouse monoclonal 24C1 raised against rhNGF) was added to each of the wells of a 96 well assay plate, the plates were wrapped in Saran wrap with a damp paper towel, and incubated overnight in a refrigerator at 2–8° C. The wells were emptied, washed 3 times using a Wheaton self filling syringe set to deliver 250 μl/well of wash buffer (containing 500 mM Tris, 2 M sodium chloride, buffered to pH 7) and patted dry. Subsequently, 200 μl of blocking buffer (1% bovine serum albumin solution) was added to each well to block nonspecific sites, 50 μl of the sample was added to each well and the plates were incubated for a minimum of 1 hour at room temperature while mixing on a platform shaker. The wells were again emptied and patted dry, and 50 μl of standard and sample solutions were added. The plates were then covered and incubated for two hours at room temperature. The wells of the plate were again emptied, washed four times with wash buffer and patted dry. Fifty (50) μl of biotinylated antibody (mouse monoclonal 8C1 raised against rh-NGF) were added to each well, the plates were covered, and incubated for two hours. The wells of the plates were emptied, washed and dried as described above and 50 μl of horseradish peroxidase-conjugated streptavidin was added to each well. The plates were covered and incubated for 20 minutes at room temperature while mixing on a platform shaker. The plates were washed five times with wash buffer. After 50 μl of orthophenylenediamine (OPD) substrate buffer were added to each well, the plates were covered and incubated in the dark for 1 hour.

A Vmax Kinetic Microplate (Molecular Devices, Mountain View) reader was used to determine the absorbance of each well. For each well, the background absorbance at 650 nm was subtracted from the peak absorbance at 450 nm to yield the net absorbance. The concentration of NGF in the samples was determined by comparison to an NGF standard curve.

Determination of NGF Activity

The bioactivity of NGF was determined by PC-12 bioassay. The PC-12 bioassay is based on increased metabolic activity of PC-12 pheochromocytoma cells (Greene, *Trends Neurosci.* 7:91, 1986) upon exposure to NGF. The metabolic activity of PC-12 cells was measured by cellular uptake of 3-[4,5 dimethylthiazol-2-yl]-2,5-diphenyltetrazoliumbromide $C_{18}H_{16}N_5Br$) (MTT), which is converted by cellular dehydrogenase into insoluble, intracellular blue crystals.

Each well of a 96-well plate contained about 30,000 PC-12 cells in 50 μl of RPMI-1640 medium. Serial dilutions of each sample and standards were prepared to produce solutions of 0.006 to 400 ng of rhNGF per ml in RPMI-1640 with 0.2% bovine serum albumin (BSA). Fifty microliters of each solution were then added to each well to yield concentrations of 0.003 to 200 ng of NGF per ml and each concentration was assayed in triplicate. After maintaining the plates for 2 days in 5% $CO_2$ at 37° C., 10 μg MTT was added to each well and the plates were incubated for an additional 4 hours. One volume of 20% SDS in 50% dimethyl formamide (DMF), pH 4.7 was then added and the plates were wrapped in cellophane, sealed inside plastic bags and incubated overnight at 37° C. The plates were read the next day using a Vmax plate reader set at 575 nm. The ratio of the $ED5_{50}$ of the sample curve to the $ED_{50}$ of a standard NGF curve provides a measure of the relative potencies of the two preparations.

EXAMPLE 1

NGF Formulation

Aqueous formulations comprising 1, 10, 100, and 1000 μg/ml rhNGF, 5 mg/ml HSA, 8.7 mg/ml sodium chloride, and 2.1 mg/ml citric acid and sufficient water to prepare 10 ml of the formulation, buffered to pH 5.2, were prepared. Following dissolution of the citric acid and salt in about 70% of the total volume, the pH was adjusted with NaOH/HCl, and the HSA and NGF added with gentle stirring along with water to make volume and the formulation filtered through a 0.2 μ Millipore Millex-GV filter.

The rhNGF used to prepare the formulations was expressed in insect cells using a baculoviral expression vector and purified by ion-exchange and reverse-phase chromatography as described in Barnett, J., et al., *Exp. Neurol.*, 110:11–24, 1990, incorporated herein by reference.

EXAMPLE 2

Stability of NGF Formulations at 5° C. and 25° C.

250 μl aliquots of a 100 μg/ml NGF formulation of Example 1 were stored at 5° C. and 25° C. (RT) in polyethylene drop-tip vials for up to 6 months. RP-HPLC, ELISA and bioassay analyses (described above) of these samples, indicated no loss of protein over 6 months (Table 1).

TABLE 1

Stability of NGF at 5° C. and 25° C. as measured by RP-HPLC, ELISA and PC-12 Bioassay.

| Storage Temp (° C.) | RP-HPLC % LS† 1 weeks | RP-HPLC % LS† 2 weeks | RP-HPLC % LS† 3 months | RP-HPLC % LS† 4 months | RP-HPLC % LS† 6 months | ELISA % LS† 6 months | Bioassay Relative Potency 6 months |
|---|---|---|---|---|---|---|---|
| 5° C. | 99 ± 2 | 99 ± 6 | 96 ± 4 | 100 ± 3 | 101 ± 3 | 100 ± 6 | 106 ± 14 |
| R.T. (22–25° C.) | 99 ± 2 | 91 ± 5 | 95 ± 5 | 103 ± 3 | 99 ± 5 | 104 ± 13 | 123 ± 3 |

†% LS = % Label Strength = $\frac{[NGF]\ test}{[NGF]\ control}$

% Relative Potency = $\frac{Activity\ test}{Activity\ control}$ (RP-HPLC numbers represent the mean ± standard deviation of 2–4 replicates. The bioassay numbers represent the mean ± 95% confidence limits of 3 determinations.)

EXAMPLE 3

Stability of Various NGF Formulations Stored in Polyethylene Catheters at 37° C.

250 μl aliquots of NGF formulations containing from 1 to 1,000 μg/ml rhNGF obtained as described in Example 1, were stored in nonradiopaque polyethylene catheters (inside diameter 0.030 inches and outside diameter 0.048 inches) at 37° C. for up to 4 weeks. The results, as shown in Table 2, indicate no significant loss of protein content (as measured by RP-HPLC), or of NGF activity (as measured by PC-12 bioassay).

TABLE 2

Stability of NGF Formulation in Polyethylene Catheters at 37° C. as determined by RP-HPLC & PC-12 Bioassay.

| [NGF] at Time Zero (μg/ml) | % LS† 1 wk RP-HPLC | % LS† 2 wks RP-HPLC | % LS† 4 wks RP-HPLC | % Relative Potency 4 wks PC-12 Bioassay |
|---|---|---|---|---|
| 1.0 | 104 ± 3 | 87 ± 6 | 85 ± 3 | 101 ± 34 |
| 10.0 | 94 ± 14 | 92 ± 4 | 100 ± 1 | 118 ± 45 |
| 100.0 | 102 ± 4 | 95 ± 6 | 95 ± 2 | 129 ± 34 |
| 1000.0 | 107 ± 2 | 92 ± 4 | 86 ± 3 | 108 ± 33 |

$$\dagger\% \text{ LS} = \% \text{ Label Strength} = \frac{[\text{NGF}] \text{ test}}{[\text{NGF}] \text{ control}}$$

$$\% \text{ Relative Potency} = \frac{\text{Activity test}}{\text{Activity control}}$$

(RP-HPLC numbers represent the mean ± standard deviation of 2–4 replicates. The bioassay numbers represent the mean ± 95% confidence limits of 3 determinations.)

EXAMPLE 4
Stability of NGF Formulation in Various Delivery Devices

The Aliquots of 100 μg/ml NGF formulation of Example 1 were filled into either an Infusaid Model 600 implantable infusion pump (Shiley-Infusaid Inc., Norwood, Mass.), a Medtronics Synchromed implantable infusion pump (Medtronics Inc., Minneapolis, Minn.) or Alzet Model 2ML 4 mini osmotic infusion pump (Alza Corp., Palo Alto, Calif.). The pumps were placed in a 37° C. water bath and the flow of formulation out of the pump was initiated. Weekly samples were collected over a 4-week period and analyzed for protein content and activity by RP-HPLC, ELISA, and PC-12 bioassay.

The data in Table 3 show that no significant decrease in NGF concentration or activity was observed.

TABLE 3

Stability of NGF formulations in various delivery devices at 37° C. for 1 month.

| Delivery System | % LS† 1 week by RP-HPLC | LS† 2 weeks by RP-HPLC | LS† 4 weeks by RP-HPLC | LS† 4 weeks by ELISA | % Relative Potency 4 weeks by Bioassay |
|---|---|---|---|---|---|
| Infusaid Model 600 Implantable Pump | 91 ± 3 | 101 ± 3 | 112 ± 4 | 90 ± 11 | 100 ± 36 |
| Medtronics Synchromed Implantable Pump | 109 ± 2 | 92 ± 2 | 91 ± 3 | 97 ± 4 | 90 ± 6 |
| Alzet 2ML4 Osmotic Minipump | 96 ± 3 | 95 ± 7 | 90 ± 5 | n.d. | n.d. |

$$\dagger\% \text{ LS} = \% \text{ Label Strength} = \frac{[\text{NGF}] \text{ test}}{[\text{NGF}] \text{ control}}$$

$$\% \text{ Relative Potency} = \frac{\text{Activity test}}{\text{Activity control}}$$

(RP-HPLC numbers represent the mean ± standard deviation of 2.4 replicates. The bioassay numbers represent the mean ± 95% confidence limits of 3 determinations.)
n.d. = not determined

EXAMPLE 5
Stability Studies of NGF Formulations at pH 4 to 10

Aqueous formulations comprising 100 μg/ml NGF, 1 mg/ml HSA, and 9 mg/ml sodium chloride, buffered at a pH of 4–10 were prepared and sterile filtered through a 0.2 μ filter (Millex-GV; Millipore Corp.). Formulations of pH 4 to 5 were 45 buffered with acetate, and formulations of pH 6–10 were buffered with Tris. Aliquots of 1 ml were transferred to polypropylene drop-tip vials, which were then incubated at either room temperature (23° to 25° C.) or 37° C. Samples were withdrawn at various time-points and analyzed by RP-HPLC. The first-order reaction rate constants, representing loss of NGF from solution, were plotted as a function of pH. The rates of NGF degradation in solution were found to increase at pH's less than about 4.5 and greater than about 6.0. The highest stability occurred at pH 5.2.

EXAMPLE 6
Stability of NGF Formulations as a Function of Carrier Concentration The type and amount of carriers were tested to determine the effect on NGF stability. A 100 μg/ml aqueous formulation as described in Example 1 and aqueous formulations comprising other carriers were prepared and are listed in Table 4. Each formulation was filter sterilized through a 0.2 μ Millipore Millex-GV filter. Stability of NGF in the various formulations was determined by incubating the NGF formulations at 37° C. in polypropylene drop-tip vials. Samples were withdrawn after 2 weeks and analyzed for protein content by RP-HPLC.

TABLE 4

Stability of various NGF formulations incubated for 2 weeks at 37° C.

| Excipient | Amount (% w/v) | % LS at 2 weeks |
|---|---|---|
| Gelatin | 1.0 | 64 ± 9 |
| Human Serum Albumin | 0.1 | 48 ± 7 |
| Human Serum Albumin | 0.5 | 99 ± 2 |
| Human Serum Albumin | 1.0 | 31 ± 36 |
| Tween 80 | 0.2 | 77 ± 9 |
| Pluronic F-68 | 0.02 | 65 ± 5 |

$$\% \text{ LS} = \text{Label Strength} = \frac{[\text{NGF}] \text{ test}}{[\text{NGF}] \text{ control}}$$

(RP-HPLC numbers represent the mean ± standard deviation of 2–4 replicates.)

EXAMPLE 7
NGF Formulation for Lyophilization

An aqueous NGF formulation comprising 100 μg/ml NGF, 30 mg/ml sucrose, 30 mg/ml mannitol, 5 mg/ml HSA and 0.3 mg/ml citric acid adjusted to pH 6.0 with NaOH was prepared at room temperature. Following dissolution of the citric acid and sugars in about 70% of the total volume, the pH was adjusted, and the HSA and NGF added with gentle stirring along with sufficient water to make volume.

EXAMPLE 8
Lyophilization of NGF Formulation

The lyophilization stability of the aqueous NGF in the formulation of Example 8 was tested. One ml aliquots of NGF formulations prepared according to Example 8 were placed in 5 ml Type I glass vials covered with lyophilization stoppers. The formulation containing vials were loaded into a freeze dryer chamber (FTS Systems Inc.), which was equilibrated at 5° C. prior to the initiation of freezing. The temperature of the chamber was then lowered to −40° C. Following a 2 hour soak at −40° C., the chamber was evacuated and the pressure was controlled at 80 to 100 milliTorr with a nitrogen sweep. A temperature ramp of 4°

C. per hour was performed until a terminal drying temperature of 25° C. was achieved. A final moisture content of between 1 and 2% of the product was attained approximately 30 hours into the cycle.

The freeze-dried powder was stored at 5° C. and reconstituted at room temperature after 3 days with 1 ml of a diluent consisting of 8.7 mg/ml sodium chloride and 1.1 mg/ml citric acid, buffered to pH 5.2. Samples were analyzed for NGF concentration by RP-HPLC. No loss of protein was observed following lyophilization.

We claim:

1. An aqueous pharmaceutical formulation comprising:
   (a) nerve growth factor;
   (b) biologically acceptable salt in an amount sufficient to maintain isotonicity;
   (c) a buffer in an amount sufficient to maintain the pH of the formulation from about 4.5 to about 6.0; and
   (d) water.

2. The aqueous pharmaceutical formulation according to claim 1 further comprising a biologically acceptable, water soluble carrier.

3. The aqueous formulation according to claim 2 wherein the carrier is human serum albumin.

4. The aqueous formulation according to claim 3, wherein the weight ratio of nerve growth factor to human serum albumin is from about 0.0001:1 to about 1:1.

5. The aqueous formulation according to claim 1, wherein the pH of the formulation is from about 5.0 to about 5.4.

6. The aqueous formulation according to claim 2, wherein:
   (a) the nerve growth factor comprises about 0.0001 to about 0.125% by weight of the aqueous formulation;
   (b) the carrier comprises about 0.1 to about 1.25% by weight of the aqueous formulation;
   (c) the salt comprises about 0.5 to about 1.0% by weight of the aqueous formulation; and
   (d) the buffer is present in an amount sufficient to maintain the pH of the aqueous formulation from about 4.5 to about 6.0.

7. The formulation according to claim 6 wherein the pH is from about 5.0 to about 5.4.

8. The aqueous formulation according to claim 6, wherein the carrier is human serum albumin, the salt is NaCl and the buffer is citric acid.

9. The aqueous formulation according to claim 8, wherein the pH is from about 5.0 to about 5.4.

10. The aqueous formulation according to claim 6 comprising 10 to 500 µg NGF, 5 mg/ml HSA, 8.7 mg/ml NaCl, 2.1 mg/ml citric acid and water, and wherein the pH of the formulation is adjusted to about 5.2.

11. A pharmaceutical formulation suitable for intravenous, intramuscular, parenteral or intracerebroventricular administration, wherein the pharmaceutical formulation comprises a sterile aqueous formulation of claim 1.

* * * * *